United States Patent [19]
Fukumoto et al.

[11] Patent Number: 5,162,596
[45] Date of Patent: Nov. 10, 1992

[54] Z-12-HEPTADECEN-1-YNE

[75] Inventors: Takehiko Fukumoto; Akira Yamamoto; Mitsuyoshi Oshima, all of Niigata, Japan

[73] Assignee: Shin-Etsu Chemical Co., Ltd., Tokyo, Japan

[21] Appl. No.: 837,025

[22] Filed: Feb. 14, 1992

[30] Foreign Application Priority Data

Feb. 19, 1991 [JP] Japan .................................. 3-46216

[51] Int. Cl.$^5$ .............................................. C07C 11/28
[52] U.S. Cl. ................................................... 585/534
[58] Field of Search ......................................... 585/534

[56]     References Cited
    FOREIGN PATENT DOCUMENTS

| 44558 | 1/1982 | European Pat. Off. | ............ | 585/534 |
| 1233237 | 9/1989 | Japan | .................................. | 585/534 |

*Primary Examiner*—Asok Pal
*Assistant Examiner*—C. Everhart
*Attorney, Agent, or Firm*—Wyatt, Gerber, Burke and Badie

[57]     ABSTRACT

Disclosed is a novel ene-yne compound Z-12-heptadecen-1-yne expressed by the structural formula $CH_3(CH_2)_3CH^{(Z)}=CH(CH_2)_9C\equiv CH$, which is useful as an intermediate in the synthetic preparation of several diene compounds having activity as a sex pheromone of the insects belonging to the lepidopteran order, such as E,Z-2,13-octadecadienyl acetate and E,Z-2,13-octadecadienal, having two double bonds at the 2- and 13-positions. The inventive compound can be synthesized by the reaction of 1-bromo-Z-10-pentadecene with sodium acetylide dispersed in an organic solvent in the presence of liquid ammonia.

1 Claim, 1 Drawing Sheet

Z-12-HEPTADECEN-1-YNE

BACKGROUND OF THE INVENTION

The present invention relates to a novel ene-yne compound not known in the prior art nor described in any literatures or, more particularly, to a novel ene-yne compound useful as an intermediate for the synthesis of several sex pheromone compounds of insects belonging to the lepidopteran order having two double bonds at the 2- and 13-positions.

SUMMARY OF THE INVENTION

The novel ene-yne compound provided by the invention is Z-12-heptadecen-1-yne expressed by the structural formula $$CH_3(CH_2)_3CH^{(Z)}=CH(CH_2)_9C\equiv CH. \qquad (I)$$

DETAILED DESCRIPTION OF THE PREFERRED EMBODIMENTS

Figure 1:
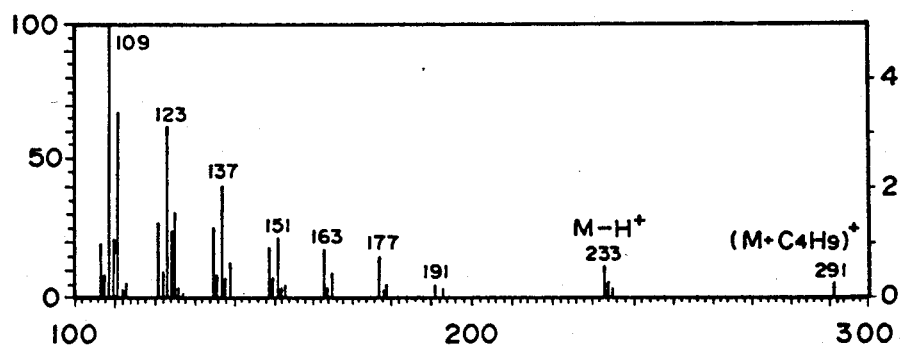
FIG. 1 is a mass spectrum of the novel compound of the present invention prepared in the Example by the CI method showing assignment of the peaks to the respective M/Z values.

The novel ene-yne compound of the invention, i.e. Z-12-heptadecen-1-yne, expressed by the above given structural formula (I) can be synthesized by several different methods. Typically, for example, the compound can be obtained by the reaction of 1-bromo-Z-10-pentadecene, which is a known compound, as the starting material with sodium acetylide dispersed in a medium containing liquid ammonia according to the following reaction equation:

$$CH_3(CH_2)_3CH^{(Z)}=CH(CH_2)_9Br + HC\equiv C-Na = CH_3(CH_2)_3CH^{(Z)}=CH(CH_2)_9C\equiv CH + NaBr.$$

Namely, sodium metal is finely dispersed in an inert solvent and acetylene is introduced into the dispersion in the presence of liquid ammonia to form sodium acetylide which is reacted with 1-bromo-Z-10-pentadecene to form the desired compound Z-12-heptadecen-1-yne. The inert solvent suitable for use here is exemplified by aromatic hydrocarbons such as toluene and xylene, aliphatic hydrocarbons such as hexane and octane and ethers such as dibutyl ether and diphenyl ether. The amount of the inert solvent to be used here is in the range from 100 to 1000 g or, preferably, from 200 to 400 g per mole, i.e. 23 g, of sodium metal.

The sodium metal should be dispersed in the inert solvent as finely as possible, preferably, to have a particle diameter not exceeding 100 μm. Acetylene gas is introduced into the dispersion of sodium metal in an amount of 1 to 3 moles or, preferably, 1.1 to 2.0 moles per mole of the sodium metal. Liquid ammonia is added to the reaction mixture in an amount of 0.2 to 2 times by volume relative to the volume of the inert solvent used in the preparation of the sodium acetylide.

The reaction mixture containing sodium acetylide is then admixed with 1-bromo-Z-10-pentadecene in an amount of 0.8 to 1.2 moles per mole of the sodium acetylide and the reaction is effected at a temperature in the range from −20° to +20° C., usually, for 1 to 5 hours. After completion of the reaction, the reaction mixture is freed from ammonia and washed with water or diluted hydrochloric acid followed by isolation of the product by a conventional procedure including the methods of solvent extraction, distillation, column chromatography and the like to give the desired Z-12-heptadecen-1-yne in a good yield which is usually in the range from 65 to 85% based on the amount of the sodium metal.

As is mentioned above, the inventive compound, Z-12-heptadecen-1-yne, can be used as an intermediate in the syntheses of several diene compounds having two double bonds at the 2- and 13-positions having activity as a sex pheromone of the insects belonging to the lepidopteran order such as E,Z-2,13-octadecadienyl acetate, which is the sex pheromone compound of *Synanthedon tipuliformis*, and E,Z-2,13-octadecadienal or so-called Koiganal-II, which is the sex pheromone compound of *Tineola bissellies*.

In the preparation of the above mentioned diene compounds, Z-12-heptadecen-1-yne is first reacted with a metal-containing basic compound to effect metallization of the acetylenic hydrogen followed by the reaction with paraformaldehyde to form Z-13-octadecen-2-yn-1-ol expressed by the structural formula $CH_3(CH_2)_3CH^{(Z)}=CH(CH_2)_9C\equiv CCH_2OH$. The metal-containing basic compound here used is exemplified by Grignard reagents such as ethylmagnesium bromide and methylmagnesium chloride, alkyl lithium compounds such as methyl lithium, n-butyl lithium, sec-butyl lithium and tert-butyl lithium and the like, of which n-butyl lithium is preferred. The basic compound is used preferably in an equimolar amount to Z-12-heptadecen-1-yne. The reaction is performed in an organic solvent such as ethers, e.g., tetrahydrofuran, diethyl ether and n-butyl ether, and hydrocarbons, e.g., hexane and toluene. The reaction with paraformaldehyde is performed at a temperature, preferably, in the range from 60° to 75° C. and the reaction is complete usually within 1 to 5 hours.

When Z-13-octadecen-2-yn-1-ol obtained in this manner is reduced with lithium aluminum hydride in an ether solvent such as diethyl ether, tetrahydrofuran and the like, E,Z-2,13-octadecadien-1-ol expressed by the structural formula $CH_3(CH_2)_3CH^{(Z)}=CH(CH_2)_9CH^{(E)}=CHCH_2OH$ is obtained. The lithium aluminum hydride is used in an amount of 0.5 to 1.1 moles per mole of the reactant ene-yne compound and the reaction is performed at a temperature of 30° to 70° C., at which the reaction is completed usually within 1 to 3 hours.

Acetylation of this dienol compound with an acetylating agent such as acetic anhydride, acetyl chloride and the like gives E,Z-2,13-octadecadienyl acetate mentioned above and expressed by the structural formula $CH_3(CH_2)_3CH^{(Z)}=CH(CH_2)_9CH^{(E)}=CHCH_2OCOCH_3$. The acetylating agent is used in an amount of at least equimolar or, preferably, from equimolar to two times by moles based on the amount of the dienol compound. The reaction is performed usually in an organic solvent such as hydrocarbons, e.g., hexane and toluene, and amine compounds, e.g., pyridine and triethyl amine, at a temperature in the range, usually, from 0° to 100° C. or, preferably, from 20° to 50° C. After completion of the reaction, the reaction mixture is washed with water and subjected to the isolation treatment of the product by the method of distillation, column chromatography and the like to give the desired E,Z-2,13-octadecadienyl acetate.

E,Z-2,13-Octadecadienal expressed by the structural formula $CH_3(CH_2)_3CH^{(Z)}=CH(CH_2)_9CH^{(E)}=CH\text{-}CHO$ can be obtained by oxidizing E,Z-2,13-octadecadien-1-ol by using a suitable oxidizing agent exemplified by pyridinium chlorochromate, chromic acid anhydride-pyridine complex, active manganese dioxide, oxidizing agents used in the so-called DMSO oxidation, e.g., the dimethyl sulfoxide-oxalyl chloride-triethyl amine system, and the like.

In the following, description is given of the synthetic preparation and characterization of Z-12-heptadecen-1-yne as the inventive compound.

tion boiling at 148° to 151° C. under a pressure of 2 mmHg.

Figure 2:
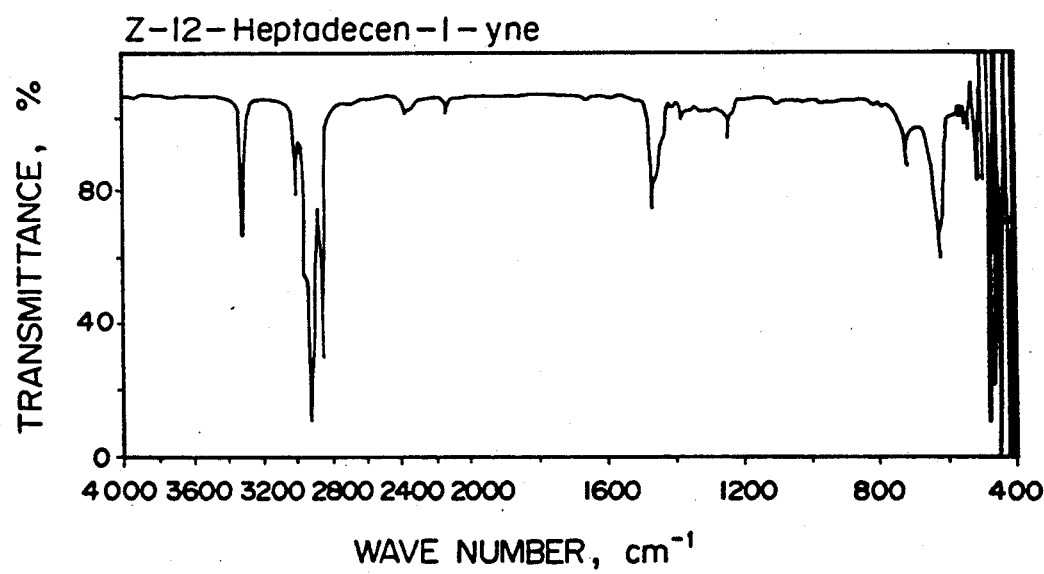
FIG. 2 is an infrared absorption spectrum of the same compound as above.

This liquid product could be identified to be Z-12-heptadecen-1-yne from the results of the mass spectrometric analysis, of which the mass spectrum is shown in FIG. 1, the infrared absorption spectrophotometric analysis, of which the absorption spectrum is shown in FIG. 2, and the $^1$H-NMR and $^{13}$C-NMR spectra, of which the data are tabulated below. The yield of the product given above corresponds to 78% of the theoretical value.

NMR data ($\delta$, ppm; in CDCl$_3$; 0.0 ppm of TMS (outer standard, taken for $^1$H-NMR and 77.0 ppm of CDCl$_3$ taken for $^{13}$C-NMR)

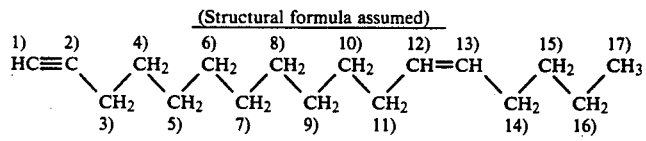

(Structural formula assumed)

EXAMPLE

Acetylene gas was blown at a flow rate of 1 liter/minute for 1 hour into a dispersion of 23 g of sodium metal having a particle diameter of 100 μm or smaller in 250 g of xylene kept at a temperature of 100° to 110° C. to give an approximately quantitative amount of sodium acetylide. This dispersion of sodium acetylide in xylene was transferred into an autoclave of 2 liter capacity and, after addition of 600 g of liquid ammonia, was kept at a temperature of −10° to −5° C. under a pressure of 3.5 to 4.0 kg/cm$^2$G. Thereafter, 289 g of 1-bromo-Z-10-pentadecene were added dropwise into the reaction mixture in the autoclave taking 1 hour and, after completion of the dropwise addition thereof, agitation of the reaction mixture was continued for additional two hours at −5° C. followed by recovery of the ammonia. The reaction mixture thus obtained was poured into an excess volume of 20% aqueous hydrochloric acid and the organic liquid taken by phase separation was freed from xylene by stripping and then subjected to distillation under reduced pressure to give 182.5 g of a fraction

| Position No. | $^1$H-NMR | $^{13}$C-NMR |
|---|---|---|
| 1) | 1.91 | 68.0 |
| 2) | — | 84.6 |
| 3) | 2.17 | 18.4 |
| 4) | 1.50 | 28.5 |
| 5) | 1.38 | 28.7 |
| 6) | 1.23–1.35 | 29.1 |
| 7) | 1.23–1.35 | 29.5 |
| 8) | 1.23–1.35 | 29.5 |
| 9) | 1.23–1.35 | 29.7 |
| 10) | 1.23–1.35 | 29.2 |
| 11) | 2.01 | 26.9 |
| 12) | 5.34 | 129.8 |
| 13) | 5.34 | 129.8 |
| 14) | 2.01 | 27.2 |
| 15) | 1.23–1.35 | 31.9 |
| 16) | 1.23–1.35 | 22.3 |
| 17) | 0.89 | 13.9 |

What is claimed is:
1. Z-12-Heptadecen-1-yne.

* * * * *